United States Patent [19]
Sunagawa et al.

[11] Patent Number: 5,279,719
[45] Date of Patent: Jan. 18, 1994

[54] METHOD FOR CHLORINATION OF METHYLATED AROMATIC COMPOUNDS

[75] Inventors: Kazuhiko Sunagawa; Hajime Hoshi; Tsumoru Watanabe, all of Iwaki, Japan

[73] Assignee: Kureha Chemical Industry Co., Ltd., Tokyo, Japan

[21] Appl. No.: 970,305

[22] Filed: Nov. 2, 1992

[30] Foreign Application Priority Data

Aug. 11, 1991 [JP] Japan .................. 3-319721

[51] Int. Cl.$^5$ .................................. C07C 17/00
[52] U.S. Cl. .......................... 204/157.6; 204/157.65; 204/157.94; 204/158.1; 204/157.99
[58] Field of Search ........... 204/157.6, 157.65, 157.94, 204/158.1, 157.99

[56] References Cited

U.S. PATENT DOCUMENTS 4,000,052 12/1976 Blumenfeld ................. 204/157.99
4,029,560 6/1977 Yoshinaka et al. ........... 204/157.99

FOREIGN PATENT DOCUMENTS 2334650 12/1976 France .
582258 12/1946 United Kingdom .

*Primary Examiner*—Donald R. Valentine
*Assistant Examiner*—Cybille Delacroix-Muirheid
*Attorney, Agent, or Firm*—Burgess, Ryan & Wayne

[57] ABSTRACT

A process for chlorination of methylated aromatic compounds in a titanium tetrachloride is disclosed. The ring chlorination is first carried out by reacting said methylated aromatic compounds with chlorine gas under reduced light conditions, and then the side chain chlorination is carried out by reacting the resulting mixture with chlorine gas under light irradiation conditions. The process ensures continuous chlorination of aromatic rings and side chains of methylated aromatic compounds at a high yield without using any catalysts or perilous solvents such as carbon tetrachloride.

6 Claims, No Drawings

METHOD FOR CHLORINATION OF METHYLATED AROMATIC COMPOUNDS

BACKGROUND OF THE INVENTION

Field of the Invention

The present invention relates to a method for chlorination of nuclei (aromatic rings) and side chains of methylated aromatic compounds.

Description of the Background Art

The reaction conditions required for chlorination of side chains and aromatic rings of methylated aromatic compounds are different. Chlorination of aromatic rings has conventionally been carried out by reacting a methylated aromatic compound with chlorine gas in the presence of a Lewis acid catalyst such as antimony chloride, ferric chloride, aluminum chloride or titanium tetrachloride, whereas chlorination of side chains has been done by reacting a methylated aromatic compound with chlorine gas under light irradiation. These chlorination reactions are usually carried out in a carbon tetrachloride solvent, or without using a solvent. When both of the aromatic rings and side chains of methylated aromatic compounds are to be chlorinated, the aromatic rings are first chlorinated in the presence of a Lewis acid catalyst, and then, after removing the catalyst, the side chains are chlorinated by subjecting the reactant to chlorine gas under light irradiation.

As to total chlorination of both the aromatic rings and side chains of methylated aromatic compounds, for example, Belgian Patent No. 631170 disclosed a method for manufacturing tetrachloro-1,3-bis-(dichloromethyl)benzene from m-xylene, which comprises i) chlorination of aromatic rings of m-xylene by reacting the m-xylene with chlorine gas in a carbon tetrachloride solvent in which ferric chloride is contained, followed by washing with water to remove the ferric chloride catalyst from the reactant; and ii) chlorination of side chains by subjecting the reactant to chlorine gas under light irradiation.

As stated above, chlorination of methylated aromatic compounds has been performed in a carbon tetrachloride solvent, which is stable under various conditions of chlorination reactions and is easy to handle owing to its low boiling point, because the resulting products of which both the aromatic rings and side chains are chlorinated become viscous or even solid. However, development of a new chlorination method in which no carbon tetrachloride is used has been desired since carbon tetrachloride is considered to contribute to the destruction of the ozone layer.

SUMMARY OF THE INVENTION

In view of this situation, the present inventors have undertaken extensive studies on the chlorination of both aromatic rings and side chains of methylated aromatic compounds, and, as a result, completed the present invention by using titanium tetrachloride as the solvent.

Furthermore, the present inventors have found that aromatic rings and side chains can be continuously chlorinated by using this solvent and by reacting the methylated aromatic compounds with chlorine gas under a shaded condition and under light irradiation.

Accordingly, an object of the present invention is to provide a method of chlorinating aromatic rings and side chains of methylated aromatic compounds using a solvent which can substitute carbon tetrachloride.

Another object of the present invention is to provide a method of continuously chlorinating both the aromatic rings and side chains of methylated aromatic compounds by simply changing the optical conditions for the chlorination.

Still another object of the present invention is to provide a method of chlorinating methylated aromatic compounds at a high yield without using any catalysts for chlorination.

The above and other objects can be achieved according to the present invention by a method of chlorinating a methylated aromatic compound characterized by reacting said methylated aromatic compound with chlorine gas in a titanium tetrachloride solvent; and by a process for chlorination of a methylated aromatic compound which comprises:

reacting said methylated aromatic compound with chlorine gas in a titanium tetrachloride solvent under a shaded or reduced light condition to effect the ring chlorination; and reacting the reactant mixture with chlorine gas in a titanium tetrachloride solvent under a light irradiation condition to effect the side chain chlorination.

Other and further objects, features and advantages of the present invention will appear more fully from the following description.

DETAILED DESCRIPTION OF THE INVENTION AND PREFERRED EMBODIMENTS

According to the present invention, the methylated aromatic compounds to be chlorinated are those having methyl group(s) attached to the carbon atom of the aromatic ring; e.g., toluene, xylene, mesitylene, metylnapthalene, and the like. In the first place, these compounds are dissolved in a titanium tetrachloride solvent and the aromatic rings of these compounds are chlorinated by injecting a specified amount of chlorine gas under a shaded condition.

The concentration of a methylated aromatic compound in the titanium tetrachloride solvent is desirably below a level where all of the intermediates and target compound do not precipitate at any point in both chlorination reactions. Nevertheless, a higher concentration is acceptable if no operational problems are encountered when precipitation of these compounds occurs. Usually, it is preferred that the chlorination reaction be carried out in a methylated aromatic compound concentration of 2-20% by weight.

Chlorination of aromatic rings is carried out under the shaded condition by feeding an amount of chlorine gas required for the chlorination into the solution of the methylated aromatic compound dissolved in titanium tetrachloride. The reaction temperature is in a range of 0°-130° C., with the preferred range being 20°-100° C. When the reaction temperature is lower than this range, the reaction rate is retarded; whereas when the temperature is higher than this range, undesirable reactions take place conspicuously. The rate of feeding chlorine gas and the reaction time vary depending on the target chlorinated products. These reaction conditions, therefore, must be determined appropriately so that the reaction can be completed in as short a time as possible so long as the exothermic heat can be controlled and the utilization of chlorine gas does not become extremely low.

The titanium tetrachloride used as a solvent also itself serves as a catalyst for ring chlorination, such that it does not necessitate any other catalysts such as ferric chloride or aluminum chloride conventionally required for chlorination of aromatic rings, and, at the same time, it does not disturb the photo-chlorination reaction. This is quite advantageous for the subsequent chlorination of methyl groups because no separation and removing procedure of catalyst is required prior to the next step. In fact, since chlorination catalysts such as ferric chloride, aluminum chloride, or the like disturb the photo-chlorination reaction in the chlorination of aromatic rings, the catalyst must be removed from the reactant solution by washing with water before the succeeding chlorination. Such a procedure can be eliminated when titanium tetrachloride solvent is adopted for use.

Consequently, the reactant mixture following ring chlorination can be fed as is to the photo-chlorination step enabling the chlorination of methyl groups.

These two chlorination reactions can be carried out in a single reaction vessel by simply switching the reaction conditions between light irradiation and the condition when light is reduced. More desirably, however, ring chlorination is performed in a shaded vessel until said chlorination is accomplished to a desired level, and then the chlorinated reaction mixture is consecutively transferred to another vessel equipped with a light irradiation device to chlorinate the methyl groups to a desired level by feeding chlorine gas into the vessel under light irradiation. Conventional light irradiation conditions generated by a high-pressure mercury lamp, low-pressure mercury lamp, gallium lamp, indium lamp and the like can be applied to this side chain chlorination, under the reaction temperature of 40°–130° C., or more preferably 50°–100° C. When the reaction temperature is lower than this range, the reaction rate is retarded; whereas when the temperature is higher than this range, undesirable subreactions markedly take place. The rate of feeding chlorine gas and the reaction time vary, in the same way as in the case of the ring chlorination under the shaded condition, depending on the target chlorinated products. These reaction conditions, therefore, must be determined appropriately so that the reaction can be completed in as short a time as possible so long as the exothermic heat can be controlled and the utilization of chlorine gas does not become extremely low.

After completing the reactions, the target product is separated from the reaction mixture by distillation to remove titanium tetrachloride. The titanium tetrachloride can easily be separated and collected by distillation. When the target compound is solidified and becomes difficult to handle due to the complete removal of titanium tetrachloride, the separation of the target compound can be facilitated by exchanging the solvents. Specifically, another inert solvent, which has a higher boiling point than titanium tetrachloride, is added to the reaction mixture from which most of the titanium tetrachloride has been removed by distillation, and the mixture is further distilled until the remaining titanium tetrachloride is almost entirely removed. The resulting solution in which no titanium tetrachloride is contained is cooled so as to precipitate the target compound. Given as examples of these solvents are o-dichlorobenzene, decalin (decahydronaphthalene), paraffin having approximately a $C_9$–$C_{12}$ content, and the like. These solvents can be used repeatedly. The target compounds thus separated are further purified by recrystallization or the like as required to proceed to the next reactions.

The chlorinated products of methylated aromatic compounds are utilized as the intermediates for useful final products such as dyestuff, agricultural chemicals, and the like. For example, tetrachloro-1,2-bis (dichloromethyl) benzene, which is a chlorinated intermediate of methylated aromatic compound of which both the benzene rings and side chains are chlorinated, can easily be converted to tetrachlorphthalide, a useful compound for agricultural chemicals, by hydrolysis in the presence of sulfuric acid.

As illustrated above, the use of titanium tetrachloride as the solvent for chlorination of both aromatic rings and methyl groups of methylated aromatic compounds assures advantages of eliminating the use of chlorination catalyst, which results in the elimination of the complicated process for the separation of catalyst following ring chlorination, and it can serve to obtain the target products at a high yield as well. Furthermore, the ring chlorination and side chain chlorination can be performed continuously, as disclosed in the present invention, if a methylated aromatic compound is first reacted with chlorine gas under the shaded condition and then reacted under the light irradiation condition.

Other features of the invention will become apparent in the following description of the exemplary embodiment which is given for illustration of the invention and is not intended to be limiting thereof.

EXAMPLE

Into a four-necked 500-ml light protective flask fitted with a gas-inlet tube, thermometer, reflux condenser and stirrer, 10.62 g (0.1 mol) of o-xylene and 419.5 g of titanium tetrachloride were charged. Chlorine gas was fed at a rate of 0.2 mol/hour into the mixture for 2 hours maintaining the bulk temperature at 40° C., with stirring. After the reaction temperature was raised to 60° C., chlorine gas was further fed at a rate of 0.1 mol/hour to complete the ring chlorination.

Chromatographic analysis of the reaction mixture revealed that the solution consisted of 70.5 mol% of 3,4,5,6-tetrachloroxylene and 25.8 mol% of 3,4,5,6,$\omega$-pentachloroxylene.

The resulting mixture was transferred to a light reaction unit fitted with a gas-inlet tube, reflux condenser and thermometer, and reacted with chlorine gas being fed at a rate of 0.1 mol/hour into the mixture for 4.5 hours, while maintaining the reaction temperature at 70° C., with stirring and light irradiation generated by a 100-W high-pressure mercury lamp.

Upon completion of the reaction, the resulting mixture was subjected to vacuum distillation at 37°–38° C. and 21 mmHg to recover 407 g of titanium tetrachloride (Recovery yield: 97%).

Chromatographic analysis revealed that the residual white solid (37.6 g) to be tetrachloro-1,2-bis (dichloromethyl) benzene having 95% purity Obviously, numerous modifications and variations of the present invention are possible in light of the above teachings. It is therefore to be understood that within the scope of the appended claims, the invention may be practiced other than as specifically described herein.

What is claimed is:

1. The method for chlorination of a methylated aromatic compound, wherein said chlorination is carried out by reacting said methylated aromatic compound with chlorine gas in a titanium tetrachloride solvent under conditions which avoid light irradiation and thereby effecting chlorination.

2. The method for chlorination of a methylated aromatic compound according to claim 1, wherein said chlorination is carried out under light irradiation conditions and thereby, effect side chain chlorination.

3. The method of claim 1 wherein the methylated aromatic compound is present in said solvent in a concentration of from about 2 to about 20% by weight.

4. The method of claim 1 wherein step (a) is conducted at a temperature of from about 0 to about 130° C. and step (b) is conducted at a temperature of from about 40 to about 130° C.

5. The method of claim 1 wherein the step (a) is conducted at a temperature of from about 20 to about 100° C. and step (b) is conducted at a temperature of from about 50 to about 100° C.

6. The method of claim 1 wherein recovery of a chlorinated methylated aromatic compound is effected by adding to the reaction mixture after completion of steps (a) and (b) and removing most of the titanium tetrachloride by distillation, an insert solvent which has a higher boiling point that titanium tetrachloride, and thereafter further distilling the mixture until the remaining titanium tetrachloride is entirely removed.

* * * * *